United States Patent [19]

Minami et al.

[11] Patent Number: 5,106,585
[45] Date of Patent: Apr. 21, 1992

[54] METHOD AND APPARATUS FOR CLEAVING DEOXYRIBONUCLEIC ACID

[75] Inventors: Tamotsu Minami, Yokosuka; Nobumi Kusuhara, Mobara; Mitsuio Onofusa, Yokohama; Toshihiro Sasaki, Kamakura, all of Japan

[73] Assignee: Mitsui Toatsu Chemicals, Inc., Tokyo, Japan

[21] Appl. No.: 672,253

[22] PCT Filed: Mar. 1, 1984

[86] PCT No.: PCT/JP84/00074
§ 371 Date: Oct. 29, 1984
§ 102(e) Date: Oct. 29, 1984

[87] PCT Pub. No.: WO84/03512
PCT Pub. Date: Sep. 13, 1984

[30] Foreign Application Priority Data
Mar. 2, 1983 [JP] Japan .................. 58-32970

[51] Int. Cl.$^5$ .............. G01N 30/02; G05B 17/00
[52] U.S. Cl. ...................... 422/68.1; 422/70; 422/116; 422/131; 422/187
[58] Field of Search ............ 435/287, 91; 422/131, 422/134, 116, 68.1, 70, 187; 935/88

[56] References Cited

U.S. PATENT DOCUMENTS

| | | | |
|---|---|---|---|
| 3,296,087 | 1/1967 | Mitsugi et al. | 536/27 X |
| 3,296,089 | 1/1967 | Nakayami et al. | 536/27 X |
| 3,531,258 | 9/1970 | Merrifield et al. | 935/88 |
| 4,353,989 | 10/1982 | Bender et al. | 435/287 |
| 4,362,699 | 12/1982 | Verlander et al. | 935/88 |
| 4,447,653 | 5/1984 | Vora | 568/697 |

OTHER PUBLICATIONS

*Chemical Engineers' Handbook*, Fifth Edition, (1973), pp. 21-60–21-62.
Proc. Natl. Acad. Sci. U.S.A., vol. 74, No. 2, pp. 560–564.

*Primary Examiner*—Carolyn S. Elmore
*Attorney, Agent, or Firm*—Burns, Doane, Swecker & Mathis

[57] ABSTRACT

The invention relates to a procedure for chemically determining the base sequence of DNA and, in particular, its step of cleaving the labeled DNA having undergone a base-selective chemical modification at the position of the modified base. More particularly, it relates to a method for cleaving DNA which comprises modifying DNA base-selectively with chemical reagents, bringing the resulting reaction mixture into contact with an adsorbent to adsorb the chemically modified DNA on the adsorbent, washing the adsorbent with a washing fluid to remove any chemical modification reagents from the adsorbent, bringing the adsorbent into contact with an eluent to elute the chemically modified DNA adsorbed thereon, concentrating the resulting eluate and then heating it together with a cleavage reagent.

This invention also relates to apparatus for carrying out the above-described method which comprises a reactor 1 for receiving the reaction mixture having undergone a chemical modification reaction of DNA, a transfer pump 4, an adsorber 2 containing an adsorbent, a three-way valve 5 and a concentrator 3, these units being interconnected by conduits in the order mentioned.

19 Claims, 2 Drawing Sheets

METHOD AND APPARATUS FOR CLEAVING DEOXYRIBONUCLEIC ACID

TECHNICAL FIELD

This invention relates to a procedure for chemically determining the base sequence of deoxyribonucleic acid and, in particular, its step of modifying radioactive phosphorus-labeled deoxyribonucleic acid base-selectively with chemical reagents and then cleaving the deoxyribonucleic acid strand at the position of the modified base. More particularly, it relates to a method for cleaving deoxyribonucleic acid by subjecting a reaction mixture containing deoxyribonucleic acid to a chemical modification reaction, separating the chemically modified deoxyribonucleic acid from the reaction mixture and then cleaving it at the position of the modified base and to apparatus for carrying out this method.

BACKGROUND ART

Recently, a number of procedures for determining the base sequence of deoxyribonucleic acid (hereinafter referred to as DNA) directly have been developed. Among others, the chemical sequence determination procedure developed by Maxam and Gilbert is being widely used because it has the advantages of involving relatively simple experimental operations and comparing favorably in rapidity and accuracy with other determination procedures. Details of this procedure are described in Proc. Natl. Acad. Sci., Vol. 74, p. 560, 1977, Tanpakushitsu-Kakusan-Koso [Protein,, Nucleic Acid and Enzyme (Japan)], Vol. 23, p. 182, 1978 and the like. Briefly stated, a DNA sample having one end labeled with radioactive phosphorus is prepared and the four bases constituting the DNA (i.e., guanine, adenine, thymine and cytosine which will hereinafter be referred to as G, A, T and C, respectively) are modified selectively with different chemical reagents. Then, with respect to each base, the DNA strand is cleaved at the position of the modified base and the resulting DNA fragments are subjected to gel electrophoresis in which the fragments are developed and separated in order of molecular chain length. By autoradiography, the developed and separated bands are recorded on an X-ray film and the bases corresponding to the bands on the X-ray film are identified to determine the base sequence of the original DNA sample.

Broadly divided, the above-described procedure can be said to comprise the following four steps:

(1) the step of labeling the 3' or 5'terminus of DNA with radioactive phosphorus;
(2) the step of chemically modifying the labeled DNA in a base-selective manner and cleaving the DNA strand at the position of the modified base;
(3) the step of developing the resulting DNA fragments by gel electrophoresis and recording the bands on an X-ray film; and
(4) the step of analyzing the bands on the X-ray film to determine the base sequence.

This Maxam-Gilbert procedure is being widely used because of its above-described advantages. However, since it has been conventional practice to carry out all of the foregoing steps by hand, determination of the base sequences of many DNA samples requires very troublesome operations and consumes much time. Therefore, it would be desirable to enhance the operating efficiency by mechanization of the steps.

Among the above-described four steps, the present invention is directed to the second step, i.e., the step of chemically modifying the labeled DNA in a base-selective manner and cleaving the DNA strand at the position of the modified base, and is concerned with a method and apparatus for mechanizing this step to enhance the operating efficiency. Conventionally, the second step has been carried out by injecting a sample solution containing the labeled DNA into four tubes made of resin, subjecting them separately to chemical modification reactions specific for four bases (i.e., G, A, T and C) using their respective reagents and reaction conditions, adding ethanol to each tube, cooling the mixture to a temperature of $-40°$ to $-70°$ C., centrifuging it and sucking out the supernatant, washing the precipitate repeatedly (by adding ethanol thereto, centrifuging the mixture and sucking out the supernatant) to remove therefrom any excess reagents used for the chemical modification, adding an aqueous solution of a cleavage reagent (sodium hydroxide or piperidine) to the precipitate and then heating the resulting mixture to cleave the DNA strand at the position of the modified base. The present inventors have concluded that, among the above-described operations, those of adding ethanol to each tube, cooling the mixture and then centrifuging it constitute a difficulty in mechanizing this step. In order to overcome the difficulty, the present inventors have made intensive studies and have found that the adsorption technique can be used in place of the centrifugation one. The present invention has been completed on the basis of this discovery.

DISCLOSURE OF THE INVENTION

According to the present invention, there is provided a method for cleaving deoxyribonucleic acid by subjecting a reaction mixture containing deoxyribonucleic acid to a chemical modification reaction, separating the chemically modified deoxyribonucleic acid from the reaction mixture, adding a cleavage reagent thereto and then heating the resulting mixture to cleave the deoxyribonucleic acid strand at the position of the modified base, characterized in that the separation procedure comprises bringing the reaction mixture having undergone the chemical modification reaction into contact with an adsorbent to adsorb the chemically modified deoxyribonucleic acid on the adsorbent, washing the adsorbent with a washing fluid to remove any chemical modification reagents from the adsorbent, bringing the adsorbent into contact with an eluent to elute the chemically modified deoxyribonucleic acid adsorbed thereon and then concentrating the resulting eluate.

According to the present invention, there is also provided apparatus for carrying out the above-described method which comprises a reactor for receiving the reaction mixture, a transfer pump, an adsorber for adsorbing and retaining the chemically modified deoxyribonucleic acid, a three-way valve and a concentrator, these units being interconnected by conduits in the order mentioned.

The above-described apparatus of the present invention can be very simply and mechanically operated by using an adsorber for adsorbing and retaining DNA from the reaction mixture having undergone a chemical modification, means for washing the adsorbed DNA to remove any reagents used for the chemical modification, means for eluting the adsorbed DNA and means for concentrating the resulting eluate, and the above-described method of the present invention can be carried out thereby.

BEST MODE FOR CARRYING OUT THE INVENTION

Figure 1:
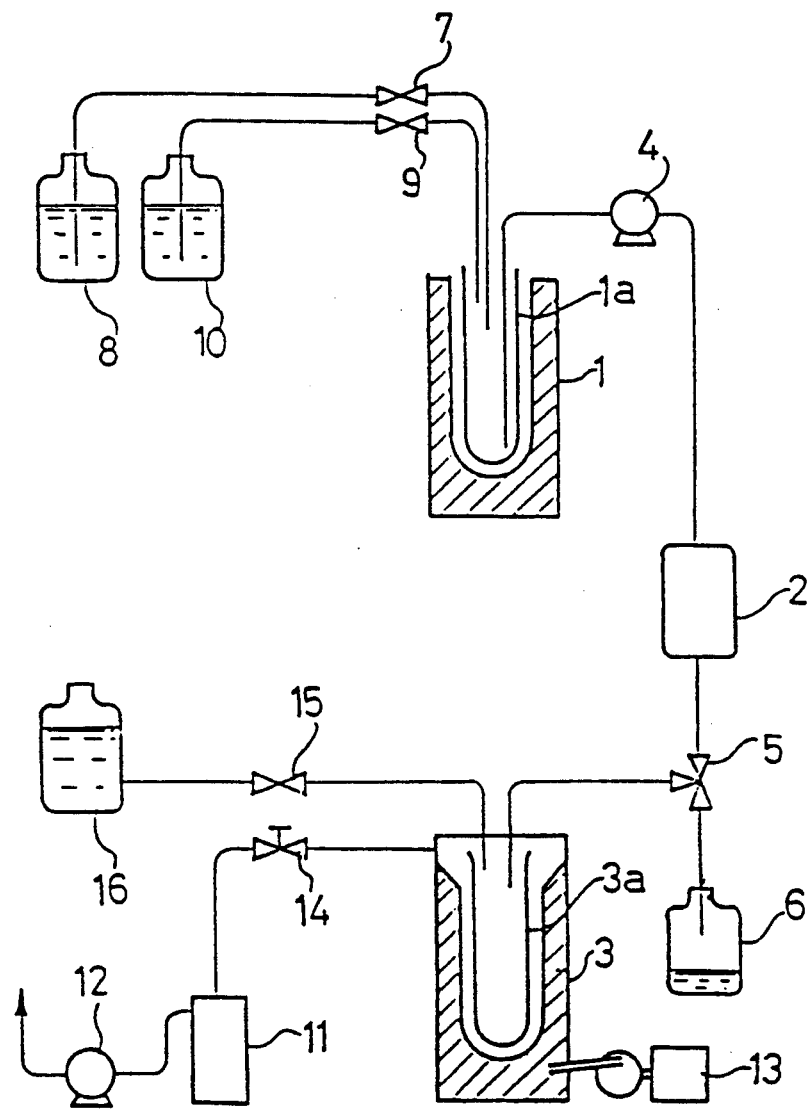
FIG. 1 is a flow diagram illustrating a preferred embodiment of the apparatus of the present invention.

In order to explain the method and apparatus of the present invention more fully, one embodiment thereof is described with reference to the accompanying drawings. In a reactor 1 shown in FIG. 1, a reaction vessel 1a is charged with radioactive phosphorus-labeled DNA, various reagents are add thereto, and the resulting reaction mixture is subjected to a chemical modification reaction at a predetermined temperature for a predetermined period of time. Thereafter, a transfer pump 4 is operated to pass the aforesaid reaction mixture through a DNA adsorber 2. The effluent from adsorber 2 is discharged into a waste liquid tank 6 via a three-way valve 5, while the chemically modified DNA is adsorbed on and retained by the adsorbent packed in adsorber 2. By opening a two-way valve 7, a predetermined amount of a washing fluid is poured into reaction vessel 1a from a washing fluid tank 8. Transfer pump 4 is operated again to conduct the washing fluid through transfer pump 4, DNA adsorber 2 and three-way valve 5 into waste liquid tank 6. Thus, any chemical modification reagents remained on the adsorbent within adsorber 2 are washed away. Then, by opening a two-way valve 9, a predetermined amount of an eluent is poured into reaction vessel 1a from an eluent tank 10. After the liquid outlet of three-way valve 5 is changed over to a concentrator 3, transfer pump 4 is operated again to conduct the eluent through transfer pump 4, DNA adsorber 2 and three-way valve 5 into a concentration vessel 3a. Thus, the chemically modified DNA adsorbed on and retained by the adsorbent within adsorber 2 is eluted and introduced into concentration vessel 3a.

A vacuum pump 12 and a vibrator 13 are operated and a vacuum regulating valve 14 is opened to concentrate the eluate within concentration vessel 3a. The evaporated liquid is collected in a trap 11. After concentrator 3 is returned to atmospheric pressure, a two-way valve 15 is opened to pour a predetermined amount of an aqueous cleavage reagent solution from an aqueous cleavage reagent solution tank 16 into concentration vessel 3a. Then, concentration vessel 3a is heated at a predetermined temperature for a predetermined period of time to obtain base-selectively cleaved DNA fragments.

As the adsorbent used in the present invention, there may be used both cation and anion exchangers. They include ones using polystyrene resin as the base material and ones using cellulose as the base material, and useful examples thereof are Dowex-X2, Dowex-50W (both are trade names; mfd. by Dow Chemical Co.), AIEC-CM52, AIEC-DE52 (both are trade names; mfd. by Whatman Co.) and the like. Moreover, there may also be used nonionic porous resins such as Amberlite XAD-2 (trade name; mfd. by Rohm & Haas Co.), Diaion HP-10 (trade name; mfd. by Mitsubishi Chemical Industries, Limited). Levacit OC1031 (trade name; mfd. by Bayer Co.) and the like. Furthermore, there may also be used fine-grainular materials adapted for reversed phase partition which, for example, include packing materials for use in high-speed liquid chromatography, such as Microbonder Pack C18, Microbonder Pack CN, Microbonder Pack-Phenyl (all are trade names; mfd. by Waters Co.) and the like.

The above-described adsorbent is usually used by packing it into a column made of glass, stainless steel or polystyrene. For example, it is preferable to use Setp Pack C-18 (trade name; mfd. by Waters Co.) or Bond Elute C-18 (mfd. by Analytichem-International Co.) which are available in the form of a packed column.

As the eluent for eluting the DNA retained by the adsorbent, there is used an aqueous solution of an acid or basic substance and preferably an aqueous solution of a volatile basic substance such as ammonia, piperazine or the like, where the adsorbent comprises an ion exchanger. Where the adsorbent comprises a nonionic porous resin or a fine-granular material adapted for reversed phase partition, a mixture of water and a volatile, water-soluble organic solvent such as methanol, ethanol or acetonitrile is used.

The reaction vessel is maintained at a predetermined temperature by means of a water bath, heater block or the like. In consideration of the fact that the reaction vessel must be discarded after each analysis because of its contamination with radioactive phosphorus, it is preferable to use disposable vessels such as Eppendorf Tube 3810 (trade name; mfd. by Eppendorf Co.).

The transfer pump serves to transfer the sample solution within the reaction vessel to the adsorber via a Teflon or silicone tube, and may comprise a tube pump having small dead space. The concentrator preferably has a construction which is adapted to contain a vessel made of glass or synthetic resin for receiving the DNA solution eluted from the aforesaid adsorbent, is provided with a temperature control means for maintaining the vessel at a constant temperature, can be hermetically sealed so as to permit a reduced pressure to be established therein, and communicates with a ventilation system. Moreover, it is more convenient to provide the concentrator with means for permitting rotation, revolution, precession or vibration of the aforesaid vessel in order to concentrate the DNA solution smoothly under reduced pressure.

As the washing fluid for washing and removing any chemical modification reagents from the adsorbent, there may be used purified water where the adsorbent comprises a cation or anion exchanger, and purified water or an aqueous solution containing not more than 10% of a water-soluble organic solvent where the adsorbent comprises a nonionic porous resin or a fine-granular material adapted for reversed phase partition.

The method of the present invention, i.e. the sequence of steps for operating the apparatus of the present invention, can be readily automated by use of a sequencer. Moreover, it is also possible to carry out the selective cleavage of DNA for four bases simultaneously by installing four vessels 3a in concentrator 3 and using four reaction vessels, adsorbers and other units arranged in parallel. The apparatus of the present invention for carrying out the method of the present invention has a simple construction requiring no expensive deep freezer or high-speed centrifuge as contrasted with conventional methods, and permits automation at low cost.

EXAMPLE

Synthetic linker a(5'-C-C-G-G-A-T-C-C-G-G-3') (Catalog No. L-1003; mfd. by Nippon Zeon Co., Ltd.) was labeled with radioactive phosphorus according to a procedure described in the literature (Tanpakushitsu-Kakusan-koso, Vol. 23, p. 182, 1978), injected into four 2-ml Eppendorf tubes (mfd. by Eppendorf Co.) in amounts of approximately 500,000 counts, and subjected to their respective chemical modification reactions. After the addition of a reaction stopper and then 1 ml of purified water, each tube was set in the reactor 1 of the apparatus illustrated in FIG. 1. Transfer pump 4 (comprising a tube pump, 1 ml/min.) was operated to pass the reaction mixture through adsorber 2 (containing the adsorbent Setp Pack C-18; mfd. by Waters Co.), which was then washed with 2 ml of purified water. Using transfer pump 4, an eluent (comprising a 40% aqueous solution of ethanol) was likewise passed through adsorber 2. By opening three-way valve 5 to concentrator 3, the resulting eluate was collected in concentration vessel 3a. After concentrator 3 was heated to 90° C., vibrator 13, vacuum pump 12 and vacuum regulating valve 14 were operated to evaporate the eluate to dryness.

Figure 2:
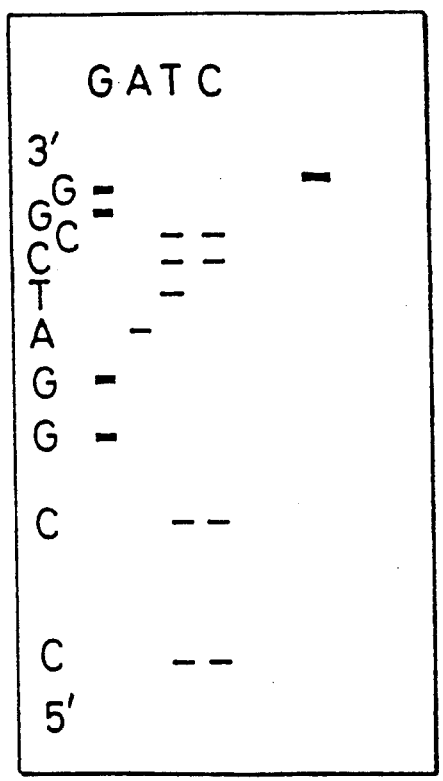
FIG. 2 is a diagram illustrating an electrophoretic autoradiogram of DNA cleaved in accordance with the present invention.

Then, by opening two-way valve 15, 0.02 ml of a 0.1 N aqueous solution of caustic soda was introduced from aqueous cleavage reagent solution tank 16 (containing a 0.1 N aqueous solution of caustic soda) into concentration vessel 3a. This concentration vessel 3a was heated at 90° C. for 30 minutes to complete the cleavage of the sample. The resulting fragments were subjected to electrophoresis using a 7 M urea-20% polyacrylamide gel and then to autoradiography. The results thus obtained are shown in FIG. 2. Analysis of this autoradiogram enables one to determine the base sequence of the sample accurately. In FIG. 2, the thick pattern seen at the right end represents an autoradiogram of the uncleaved sample.

What is claimed is:

1. Apparatus for cleaving deoxyribonucleic acid, which comprises:
   (a) a reactor containing a reaction mixture comprising deoxyribonucleic acid which is to be subjected to a chemical modification reaction, whereby at least one base of the deoxyribonucleic acid is chemically modified;
   (b) a transfer pump connected by conduit to said reactor for bringing said reaction mixture having undergone a chemical modification reaction into contact with an adsorber;
   (c) an adsorber connected by conduit to said transfer pump, said adsorber comprising an adsorbent for adsorbing and retaining the chemically modified deoxyribonucleic acid, said adsorber further comprising washing means for washing the adsorbent with a washing fluid to remove any chemical modification reagents from said adsorbent, said adsorber further comprising eluting means for eluting chemically modified deoxyribonucleic acid from the adsorbent; and
   (d) a concentrator connected by conduit to said adsorber for concentrating DNA eluates received from the adsorber, said concentrator further comprising cleavage reagent supplying means for adding cleavage reagent to the concentrator, said concentrator further comprising heating means for heating the cleavage reagent and DNA eluates, whereby the deoxyribonucleic acid is cleaved at the position of the modified base.

2. Apparatus as claimed in claim 1 wherein said adsorber is packed with an adsorbent selected from the group consisting of ion exchanges, nonionic porous resins and fine-granular materials adapted for reversed phase partition.

3. Apparatus as claimed in claim 1 wherein said concentrator is adapted to be capable of controlling the concentration vessel at an arbitrarily selected temperature and subatmospheric pressure and permit rotation, revolution, precession and vibration of said vessel.

4. Apparatus as claimed in claim 1 wherein the operation of the apparatus is automated by means of a sequencer for elements (a) to (d) of the apparatus.

5. Apparatus for the selective cleavage of DNA for four bases simultaneously, comprising four reaction vessels in concentrator (d) of claim 1 and three sets of elements (a) to (c) of claim 1 arranged in parallel.

6. An apparatus for determining the base sequence of deoxyribonucleic acid comprising:
   (a) a reaction vessel containing a reaction mixture comprising radioactive phosphorous-labeled DNA;
   (b) a DNA adsorber attached to said vessel, said DNA adsorber further comprising an adsorbent for adsorbing DNA;
   (c) means for washing adsorbed DNA to remove any reagents used for chemical modification;
   (d) means for eluting the adsorbed DNA from the adsorbent, whereby an eluate is obtained;
   (e) a concentrator attached to said adsorber for collecting and concentrating the eluate;
   (f) means for introducing a cleavage reagent attached to said concentrator whereby modified DNA strands located in said concentrator can be cleaved where modified bases are positioned to provide DNA fragments.

7. The apparatus of claim 6 further comprising a conduit between said vessel and said adsorber and a transfer pump located on said conduit for transferring fluids to said adsorber.

8. The apparatus of claim 7 further comprising a waste liquid tank connected by conduit to said adsorber for collecting effluent from said adsorber.

9. The apparatus of claim 8 wherein said adsorber has inlet and outlet means, and wherein said conduit attached to said waste liquid tank is connected to said outlet means.

10. The apparatus of claim 9 wherein said conduit attached to said waste liquid tank is provided with a three-way valve.

11. The apparatus of claim 10 wherein said concentrator is connected to said adsorber by a conduit connected to said three-way valve.

12. The apparatus of claim 11 where the concentrator further comprises a vessel for collecting an eluate from said adsorber, a vacuum pump, a vibrator, heating means and a trap for collecting evaporated liquid.

13. The apparatus of claim 12 wherein said means for washing is a washing fluid tank containing washing fluid connected by conduit to said reaction vessel, said means for washing further comprising a two-way valve located on the conduit connecting said washing fluid tank to said reaction vessel, whereby flow of the washing fluid is controlled.

14. The apparatus of claim 13 wherein said means for eluting is an eluent tank containing eluent connected by conduit to said reaction vessel, said eluent tank further comprising a two-way valve located on the conduit connecting said eluent tank to the reaction vessel, whereby flow of the eluent is controlled.

15. The apparatus of claim 14 wherein said means for introducing a cleavage reagent is a cleavage reagent tank containing a cleavage reagent connected by conduit to said concentrator, said cleavage reagent tank further comprising a two-way valve located on said conduit connecting said cleavage reagent tank to said concentrator, whereby flow of the cleavage reagent is controlled.

16. The apparatus of claim 6 wherein the adsorbent comprises cation, anion or nonionic porous resins.

17. The apparatus of claim 6 wherein the adsorbent comprises polystyrene as base material, cellulose as base material, AMBERLITE XAD-2 or LEVACIT OC1031.

18. Apparatus as claimed in claim 6 wherein the operation of the apparatus is automated by means of a sequencer for elements (a) to (f) of the apparatus.

19. Apparatus for the selective cleavage of DNA for four bases simultaneously, comprising four reaction vessels in concentrator (e) of claim 6, means (f) of claim 6 can separately deliver to each of the four reaction vessels in concentrator (e), and three sets of elements (a) to (d) of claim 6 arranged in parallel.

* * * * *